United States Patent [19]

Sajtos

[11] Patent Number: 5,015,760
[45] Date of Patent: May 14, 1991

[54] PROCESS FOR THE PREPARATION OF GLYOXYLIC ACID AND GLYOXYLIC ACID DERIVATIVES

[75] Inventor: Alexander Sajtos, Linz, Austria

[73] Assignee: Chemie Linz Aktiengesellschaft, Linz, Austria

[21] Appl. No.: 331,026

[22] Filed: Mar. 29, 1989

Related U.S. Application Data

[63] Continuation of Ser. No. 508,054, Jun. 24, 1983, abandoned.

[30] Foreign Application Priority Data

Jul. 2, 1982 [DE] Fed. Rep. of Germany ....... 3224795

[51] Int. Cl.$^5$ .............................................. C07C 69/66
[52] U.S. Cl. ..................................... 560/186; 562/587
[58] Field of Search ......................... 560/186; 562/587

[56] References Cited

U.S. PATENT DOCUMENTS

| | | | |
|---|---|---|---|
| 3,145,232 | 8/1964 | Thompson | 562/577 |
| 3,637,721 | 10/1972 | Pappas | 562/577 |
| 3,705,922 | 1/1972 | Callighan | 562/587 |

OTHER PUBLICATIONS

CRC Handbook of Chemistry and Physics, 60th Ed. (1979–1980), CRC Press. p. D-149.

Deslongchamps, Pierre *Stereoelectronic Effects in Organic Chemistry* Pergamon Press (1983), pp. 41–471.

*Primary Examiner*—Paul J. Killos
*Attorney, Agent, or Firm*—Wenderoth, Lind & Ponack

[57] ABSTRACT

Preparation of glyoxylic acid or derivatives thereof of the formula

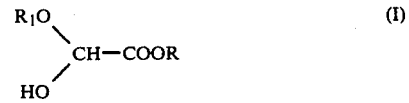

in which R denotes an alkyl radical with 1 to 10 C atoms and $R_1$ denotes an alkyl radical with 1 to 4 C atoms, by ozonolysis of a dialkyl maleate, in which the alkyl radicals each have 1 to 10 C atoms, with the equivalent amount of ozone in an aliphatic alcohol of the formula $R_1OH$, and subsequent catalytic hydrogenation, in which the ozonolysis product is continuously introduced into a suspension of the hydrogenation catalyst in the alcohol of the formula $R_1OH$ such that the peroxide content of the hydrogenation solution is not more than 0.1 mole/liter during the hydrogenation. Glyoxylic acid can be obtained from the resulting acetals of the formula I by hydrolysis.

15 Claims, No Drawings

PROCESS FOR THE PREPARATION OF GLYOXYLIC ACID AND GLYOXYLIC ACID DERIVATIVES

This application is a continuation of Ser. No. 508,054, filed June 24, 1983, now abandoned.

The invention relates to a process for the preparation of hemi-acetals of alkyl glyoxylates or glyoxylic acid by ozonolysis of an alkyl maleate and subsequent catalytic hydrogenation of the ozonolysis product.

The preparation of carbonyl compounds from unsaturated organic carbon compounds with one or more olefinic double bonds in the molecule by means of an ozonolysis and reduction process is known When this method is applied, the reduction always presents difficulties, since the peroxide-containing ozonolysis products are unstable and undergo rearrangement reactions particularly readily in the presence of metallic hydrogenation catalysts before they can be reduced to the corresponding carbonyl compounds. In addition, if noble metal catalysts are in contact with peroxide-containing solutions, losses in the activity of the catalyst are observed. Substantial losses in yield and difficulties in preparing the end products in a pure form thereby arise.

To avoid these difficulties, U.S. Pat. No. 3,145,232 recommends a process in which the reduction is carried out immediately after the ozonolysis, at temperatures below −40° C. in the presence of equivalent amounts of a trialkyl phosphite. Besides the expenditure on apparatus to obtain the extremely low reaction temperatures, such a reaction procedure requires the use of absolutely anhydrous solvents, since trialkyl phosphites are hydrolyzed extremely rapidly in water-containing solvents. Moreover, separation of the free carbonyl compounds from the phosphate esters formed during the reduction presents considerable difficulties.

Since it has been found that low reaction temperatures have an adverse effect on the activity of the reducing agents used and losses in yield therefore arise, in a process such as is described in U.S. Pat. No. 3,637,721 ozonolysis of the olefinic double bond is indeed carried out at temperatures of −50° C., but the reaction temperatures are increased up to 50° C. in the course of reduction with aliphatic or aromatic disulfides. For the preparation of glyoxylic acid by ozonolysis of maleic acid and reduction of the ozonolysis product with dimethyl sulfide, a yield of 91% is given, but this is obtained by formation of the insoluble 2,4-dinitrophenylhydrazine derivative of glyoxylic acid, since free glyoxylic acid cannot be separated off from the dimethylsulfoxide formed. The preparation of hemi-acetals of alkyl glyoxylates from ethyl maleate or methyl maleate is also described in the above specification, but separation of the hemi-acetals of alkyl glyoxylates from dimethylsulfoxide after the reduction is likewise only incomplete.

U.S. Pat. No. 3,705,922 thus describes an improved process for the preparation of glyoxylic acid hemi-acetals in which maleic acid is reacted with an excess of ozone and the peroxide-containing ozonolysis products are reduced by catalytic hydrogenation in the presence of palladium on an aluminum oxide support.

Although in the latter process it is not necessary to apply low temperatures or to use expensive, toxic and foul-smelling reducing agents, removal of which, after conversion into the oxidized form, from the reaction mixture is impossible or difficult, the use of a very expensive and specific catalyst material, on the other hand, must be accepted. Since noble metal catalysts are deactivated on prolonged contact with organic peroxides, the yield of the hydrogenation reaction here depends on the amount and composition of the hydrogenation catalyst. As can be seen from a comparison of the examples in U.S. Pat. No. 3,705,922, the yield decreases by about 10%, in spite of an appropriately extended reaction time, if, for the same batch size, only 0.2 g of the Pd/Al2O3 catalyst is used, instead of 0.5 g. The process becomes completely uneconomical if a conventional catalyst, such as Pd/charcoal, is used instead of a palladium catalyst with aluminum oxide as the support. In addition, U.S. Pat. No. 3,705,922 contains no statements regarding regeneration and re-usability of the spent catalyst material. Surprisingly, the disadvantages of the known processes can be avoided, according to the present invention, by a process in which one molar equivalent of ozone is used for ozonolytic splitting of the olefinic double bond and the peroxide-containing ozonolysis products are very rapidly reduced by catalytic hydrogenation in dilute alcoholic solution with a very low concentration of peroxides.

The invention accordingly relates to a process for the preparation of glyoxylic acid or derivatives thereof of the general formula

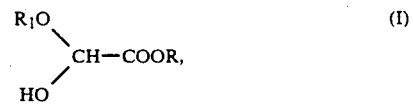

in which R denotes an alkyl radical with 1 to 10 C atoms and $R_1$ denotes an alkyl radical with 1 to 4 C atoms, comprising (a) dissolving of a dialkyl maleate in which the alkyl radicals each have 1–10 C atoms in an aliphatic alcohol of the formula $R_1OH$, in which $R_1$ has the abovementioned meaning, and reaction of the maleate thus dissolved with the equivalent amount of ozone at −80° to +20° C., and (b) catalytic hydrogenation of the peroxide-containing solution thus obtained, under a pressure of 1 to 20 bar, at a temperature of 15° to 45° C. and at a pH value of 2 to 7, this peroxide-containing solution being introduced continuously into a suspension of a catalyst, suitable for catalytic hydrogenation, in the alcohol of the formula $R_1OH$, in which $R_1$ is as defined above, in a dosage such that a peroxide content of not more than 0.1 mole/liter is established and maintained in the mixture to be hydrogenated throughout the entire course of the hydrogenation, after which the hemi-acetal of alkyl glyoxylate of the formula I formed (i) is isolated or (ii) is hydrolyzed to glyoxylic acid, with or without prior isolation from the reaction mixture.

Because they are readily accessible, dimethyl maleate and diethyl maleate are preferably used as starting materials for the process according to the invention. However, the higher alkyl esters, for example the dibutyl or dioctyl ester, are also likewise suitable. It is also possible to esterify maleic anhydride in the presence of a lower aliphatic alcohol under acid catalysis, for example by addition of a strongly acid ion exchanger in the H form or catalytic amounts of a mineral acid, and to subject the solution of the corresponding dialkyl maleate thereby formed directly to ozonolysis. In this procedure, it should be ensured that esterification of the maleic anhydride is as complete as possible.

The ozonolysis is preferably carried out at temperatures from −20° C. to +10° C., and the temperature is again particularly preferably kept within the range from −10° to +5° C. In the process according to the invention, the dialkyl maleate is reacted with the equivalent amount of ozone, the ozone being taken up quantitatively and stoichiometric amounts of the particular dialkyl maleate used being consumed under the given process conditions. When the ozonization has ended, no measures to drive off excess or unreacted ozone from the reaction mixture before the hydrogenation are therefore required.

The lower aliphatic alcohol used as the solvent in the ozonolysis and hydrogenation is important inasmuch as this alcohol participates in the acetal formation of the hemi-acetal of alkyl glyoxylates of the formula I. The reaction sequence can be shown schematically by the following equation summary, in which R and $R_1$ have the same meaning as in formula I:

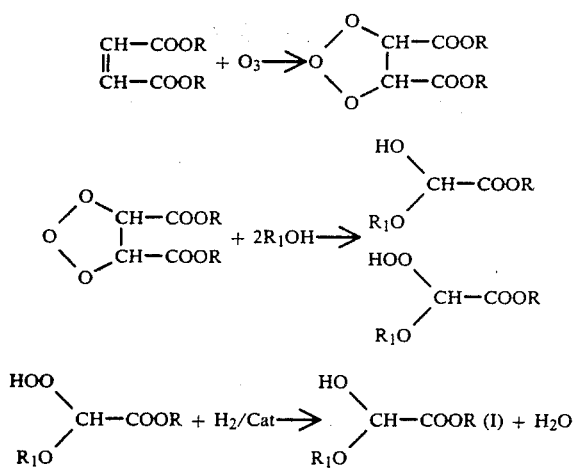

Methanol and ethanol are particularly suitable alcoholic solvents of the formula $R_1OH$ for carrying out the ozonolysis and hydrogenation, and the use of methanol is again particularly preferred.

In the process according to the invention, the catalytic hydrogenation of the ozonolysis products is carried out in very dilute alcoholic solution, care being taken, by the measures described below, that a peroxide content of not more than 0.1 mole/liter, preferably of not more than 0.05 mole/liter and in particular of not more than 0.02 mole/liter, is established and maintained throughout the entire hydrogenation. For this, a suspension of the catalyst in the alcohol of the formula $R_1OH$ used as the solvent in the ozonolysis is introduced into a hydrogenation reactor and the solution obtained in the ozonization is fed in continuously by means of an adjustable metering device. During addition of the ozonolysis solution at the start and in the course of the hydrogenation, care should of course be taken that the abovementioned peroxide content in the hydrogenation reactor is not exceeded by the amount of peroxide-containing ozonolysis products fed in.

Rapid reduction is ensured by the low concentration of peroxide-containing ozonolysis solution in the reaction medium during the actual hydrogenation operation as a result of continuous feeding. In this manner, poisoning of the catalyst and the loss in activity associated therewith is prevented. Overall, however, a large amount of ozonolysis products can be reduced in a relatively small volume by the continuous addition, which means that high concentrations of hemi-acetals of alkyl glyoxylates are formed and time and expense in distillative removal of the solvents are saved.

Suitable catalysts are the noble metal catalysts which are suitable for hydrogenation reactions, and they can be used in the form of powdered catalysts with supports or without a support. Palladium or platinum catalysts, especially platinum catalysts without a support, are preferably used. In the case of powdered catalysts, examples of suitable supports are charcoal, aluminum oxide, silica gel and kieselguhr. The yields in the process according to the invention are in principle independent of the amount of catalyst used, however, in order to achieve a sufficient rate of hydrogenation, it is advisable to introduce the above catalysts in noble metal amounts of 0.1 to 5% by weight, preferably of 0.5 to 2% by weight, based on the particular total amount of ozonized dialkyl maleate fed in per hour.

When the reduction has ended, the catalyst is removed from the reaction mixture and used for further hydrogenations without regeneration, no loss in activity of the catalyst being observed.

Equivalent amounts of hydrogen are consumed for reduction of the ozonolysis products in the process according to the invention. The amount of hydrogen which can be used in the hydrogenation ranges from one molar equivalent up to a several-fold molar excess. The use of excess hydrogen in principle provides no advantages, and is only expedient in order to ensure adequate supply of the hydrogenation mixture with hydrogen.

The hydrogenation in the process according to the invention is advantageously carried out under virtually atmospheric pressure conditions. In this context, virtually atmospheric pressure conditions are understood as meaning pressures of 1 to about 3 bar, as is customary in industry in order to prevent infiltration of air into the hydrogenation reactor. The reduction of the ozonolysis products is technically very simple to carry out in this manner. However, it is also possible to carry out the hydrogenation under a pressure of up to 20 bar and thereby to increase the rate of hydrogenation.

The reduction proceeds exothermically and, according to a preferred embodiment of the present invention, is carried out at temperatures of 20° to 40° C., in particular at temperatures in the range from 35° to 40° C., a pH value of 2 to 4 preferably being maintained.

Since small amounts of acid by-products are formed in the course of the hydrogenation, to maintain the pH value during the hydrogenation, continuous adjustment by metered addition of a base, for example NaOH, is necessary. The base which is then present in bonded form in the hydrogenation mixture is advantageously removed, for example by binding with a mineral acid, before isolation of the hemi-acetal of the formula I.

The hemi-acetals of alkyl glyoxylates of the formula I prepared by the process according to the invention are in dynamic equilibrium with the corresponding acetals of alkyl glyoxylates and hydrates of alkyl glyoxylates, according to the following schematic equation summary, in which R and $R_1$ have the same meaning as in formula I:

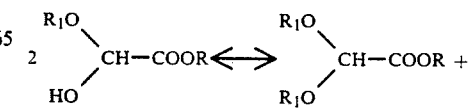

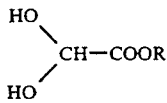

The hemi-acetals of alkyl glyoxylates of the formula I are useful starting materials for obtaining glyoxylic acid. For example, the hemi-acetals of alkyl glyoxylates can be hydrolyzed quantitatively to glyoxylic acid by heating in water and distilling off the alcohol formed. The hydrolysis can be accelerated in the conventional manner by addition of catalytic amounts of acids or addition of bases.

However, it is not necessary here to isolate the hemi-acetals of alkyl glyoxylates after the hydrogenation, since the hydrolysis can be carried out in a cost-saving and time-saving manner directly in the hydrogenation solution after the hydrogenation has ended and the catalyst has been removed.

The process according to the invention is illustrated in the following examples.

EXAMPLE 1

900 g (6.25 moles) of dimethyl maleate in 4 liters of methanol are introduced into a bubble column. Ozonization is carried out with an air/ozone mixture (3 m$^3$/hour of air, 30 g of $O_3$/m$^3$) for 3 hours and 20 minutes, with cooling to 0° to 4° C. The ozone is thereby quantitatively taken up and, when the ozonolysis has ended, the residual content of dimethyl maleate is less than 1% of the amount of dimethyl maleate originally present.

The solution obtained in the ozonolysis is divided into portions and is fed into a hydrogenation reactor, into which a suspension of 1.5 g of Pt in 0.5 liter of methanol has been introduced and which has been filled with hydrogen, via a metering vessel in doses such that the peroxide content in the hydrogenation reactor at the start and in the course of the entire hydrogenation is not more than 0.1 mole/liter. Hydrogenation is continued, with vigorous stirring and with addition of hydrogen, until a sample shows a negative peroxide test, a temperature of 30° C.–40° C. and, by addition of methanolic NaOH, a pH value of 2 to 4 being maintained throughout the entire hydrogenation period.

The contents of the hydrogenation reactor are then filtered off with suction over a frit down to a residue of 0.5 liter, more ozonized solution is fed into the reactor via the metering vessel and the hydrogenation operation is repeated under the abovementioned reaction conditions.

When the hydrogenation has ended, the methyl hemi-acetal of methyl glyoxylate content is determined polarographically as 12.125 moles (97% of theory).

For further processing, the NaOH present in bonded form in the hydrogenation mixture is carefully precipitated as $Na_2SO_4$ with 98% strength $H_2SO_4$, with cooling, and the $Na_2SO_4$ is separated off by filtration. The methanol is then removed on a Rotavapor and the residue is distilled at about 55° C. under 25 mm Hg. The yield of pure methyl hemi-acetal of methyl glyoxylate is 1,425 g (11.87 moles), corresponding to 95% of theory.

EXAMPLE 2

21.6 g (150 mmoles) of dimethyl maleate in 100 ml of methanol are introduced into a reactor. Ozonization is carried out with an $O_2/O_3$ mixture (60 liters of $O_2$/hour, 1.66 g of $O_3$/hour) for 4 hours and 20 minutes, with cooling to 0° to 3° C. The ozone is thereby quantitatively taken up, and a stoichiometric amount of dimethyl maleate is consumed. Ozonization is carried out until the residual content of dimethyl maleate is less than 1% of the amount originally present.

The solution obtained in the ozonolysis is fed, with stirring and while passing in hydrogen, into a hydrogenation reactor, into which a suspension of 0.1 g of platinum in methanol has been introduced, via a metering vessel in doses such that the peroxide content in the hydrogenation reactor at the start and in the course of the hydrogenation does not exceed 0.02 mole/liter. The reaction mixture is kept at 20° C. by external cooling and a pH value of 4 to 5 is established by addition of methanolic NaOH. When the addition of the ozonolysis solution has ended, the reaction mixture is peroxide-free within 5 minutes. The catalyst is then removed by filtration and used for further hydrogenation reactions.

Determination of the content by means of oxime titration and polarography shows a 96% yield of the methyl hemi-acetal of methyl glyoxylate, based on dimethyl maleate.

The methyl hemi-acetal of methyl glyoxylate is isolated as described in Example 1.

EXAMPLE 3

612.5 g (6.25 moles) of maleic anhydride are dissolved in 4 liters of methanol and esterified under acid catalysis by addition of a strongly acid ion exchanger in the H form. Ozonolysis and hydrogenation are carried out as described in Example 1. The yield of methyl hemi-acetal of methyl glyoxylate is 94% of theory.

EXAMPLE 4

25.83 g of diethyl maleate are dissolved in 100 ml of methanol and ozonized. Ozonolysis and hydrogenation are carried out under the conditions described in Example 2. 39.1 g (292 mmoles) of methyl hemi-acetal of ethyl glyoxylate are thus obtained, corresponding to a yield of 97.3% of theory.

EXAMPLE 5

34.25 g of di-n-butyl maleate are dissolved in 100 ml of methanol and ozonized. Ozonolysis and hydrogenation are carried out under the conditions described in Example 2. 46.8 g (289 mmoles) of the methyl hemi-acetal of n-butyl glyoxylate are thus obtained, corresponding to a yield of 96.3% of theory.

EXAMPLE 6

34.25 g (150 mmoles) of di-n-butyl maleate are diluted to 100 ml with n-butanol and reacted with 150 mmoles of ozone as in Example 2. After hydrogenation under the conditions described in Example 2, 42.55 g (208.6 mmoles) of the n-butanol hemi-acetal of n-butyl glyoxylate are obtained, corresponding to a yield of 81.25% of theory.

EXAMPLE 7

51.08 g of di-n-octyl maleate are dissolved in 100 ml of methanol and ozonized. Ozonolysis and hydrogenation are carried out under the conditions described in Example 2. For working up, the catalyst is removed by filtration when the hydrogenation has ended, water is added to the filtrate and the mixture is neutralized with dilute $H_2SO_4$. Methyl hemi-acetal of n-octyl glyoxylate thereby separates out as an organic phase, which is washed, dried and distilled in vacuo. 61.9 g (284 mmoles) of methyl hemi-acetal of n-octyl glyoxylate are thus obtained, corresponding to a yield of 94.6% of theory.

EXAMPLE 8

21.6 g (150 mmoles) of dimethyl maleate are made up to 100 ml with methanol and reacted with 150 mmoles of ozone as in Example 2. The solution obtained in the ozonolysis is fed, via a metering vessel, into a hydrogenation reactor, into which a suspension of a 10% strength Pd catalyst on charcoal has been introduced, and hydrogenation is carried out under the conditions described in Example 2. After less than 10 minutes, the mixture is free from peroxide.

Determination of the content by polarography shows a methyl hemi-acetal of methyl glyoxylate content of 243.8 mmoles, corresponding to a yield of 81.25% of theory.

EXAMPLE 9

85 g (0.7 mole) of 98.5% pure methyl hemi-acetal of methyl glyoxylate are heated with 100 g of $H_2O$ until 55 g of methanol/water distillate have passed over at a bottom temperature of 105° C.. 130 g of aqueous glyoxylic acid solution containing 0.69 mole of glyoxylic acid remain.

The hemi-acetals according to Examples 4, 5, 6 and 7 can also be hydrolyzed to glyoxylic acid in a similar manner.

What I claim is:

1. In a process for the preparation of glyoxylic acid derivatives of the formula

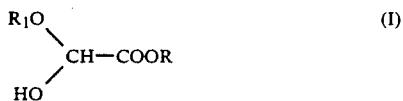

in which R denotes an alkyl radical with 1 to 10 C atoms and $R_1$ denotes an alkyl radical with 1 to 4 C atoms, comprising (a) dissolving of a dialkyl maleate in which the alkyl radicals each have 1–10 C atoms in an aliphatic alcohol of the formula $R_1OH$, in which $R_1$ has the abovementioned meaning, and reaction of the maleate thus dissolved with the equivalent amount of ozone at −80° to +20° C., and (b) catalytic hydrogenation of the peroxide-containing solution thus obtained, under a pressure of 1 to 20 bar, at a temperature of 15° to 45° C., after which the hemi-acetal of alkyl glyoxylate of the formula I formed is isolated, the improvement wherein
(i) said peroxide-containing solution is continuously introduced into a vessel containing a suspension of a noble metal catalyst suitable for the catalytic hydrogenation, in the alcohol of the formula $R_1OH$, in which $R_1$ is as defined above, in the presence of hydrogen and said peroxide-containing solution being added at such rate that a peroxide content of not more than 0.1 mole/liter is established and maintained in the mixture to be hydrogenated throughout the entire course of the hydrogenation and
(ii) the pH of said hydrogenation is maintained at 2 to 7.

2. The process as claimed in claim 1, in which the ozonolysis in stage (a) is carried out at temperatures in the range from −10° to +5° C.

3. The process as claimed in claim 1, in which methanol is used as the alcohol of the formula $R_1OH$.

4. The process as claimed in claim 1, in which a peroxide content of not more than 0.02 mole/liter is established and maintained in the hydrogenation reactor throughout the entire hydrogenation in stage (b).

5. The process as claimed in claim 1, in which a support-free platinum catalyst is used in the hydrogenation in stage (b).

6. The process as claimed in claim 1, in which a temperature of 35° to 40° C. is maintained during the hydrogenation in stage (b).

7. The process as claimed in claim 1, in which a pH value of 2 to 4 is maintained during the hydrogenation in stage (b).

8. In a process for the preparation of glyoxylic acid comprising (a) dissolving of a dialkyl maleate in which the alkyl radicals each have 1–10 C atoms in an aliphatic alcohol of the formula $R_1OH$, in which $R_1$ is as defined in claim 1, and reaction of the maleate thus dissolved with the equivalent amount of ozone at −80° to +20° C. and (b) catalytic hydrogenation of the peroxide-containing solution thus obtained, under a pressure of 1 to 20 bar, at a temperature of 15° to 45° C., after which the hemi-acetal of alkyl glyoxylate of the formula I formed is hydrolyzed to glyoxylic acid, with or without prior isolation from the reaction mixture, the improvement wherein
(i) said peroxide-containing solution is continuously introduced into a vessel containing a suspension of a noble metal catalyst suitable for the catalytic hydrogenation, in the alcohol of the formula $R_1OH$, in which $R_1$ is as defined above, in the presence of hydrogen and said peroxide-containing solution being added at such rate that a peroxide content of not more than 0.1 mole/liter is established and maintained in the mixture to be hydrogenated throughout the entire course of the hydrogenation and
(ii) the pH of said hydrogenation is maintained at 2 to 7.

9. The process as claimed in claim 8, in which the ozonolysis in stage (a) is carried out at temperatures in the range from −10° to +5° C.

10. The process as claimed in claim 8, in which methanol is used as the alcohol of the formula $R_1OH$.

11. The process as claimed in claim 8, in which a peroxide content of not more than 0.02 mole/liter is established and maintained in the hydrogenation reactor throughout the entire hydrogenation in stage (b).

12. The process as claimed in claim 8, in which a support-free platinum catalyst is used in the hydrogenation in stage (b).

13. The process as claimed in claim 8, in which a temperature of 35° to 40° C. is maintained during the hydrogenation in stage (b).

14. The process as claimed in claim 8, in which a pH value of 2 to 4 is maintained during the hydrogenation in stage (b).

15. The process as claimed in claim 8, in which the hydrolysis to glyoxylic acid is carried out by heating the hemi-acetal of alkyl glyoxylate of formula I with water and distilling off the alcohol/water mixture.

* * * * *